(12) United States Patent
Mihashi et al.

(10) Patent No.: US 7,249,852 B2
(45) Date of Patent: Jul. 31, 2007

(54) EYE CHARACTERISTIC MEASURING APPARATUS

(75) Inventors: Toshifumi Mihashi, Tokyo (JP); Yoko Hirohara, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 679 days.

(21) Appl. No.: 10/648,827

(22) Filed: Aug. 27, 2003

(65) Prior Publication Data
US 2005/0099599 A1  May 12, 2005

(30) Foreign Application Priority Data
Aug. 29, 2002  (JP) .............................. 2002-250126

(51) Int. Cl.
*A61B 3/10*  (2006.01)
(52) U.S. Cl. ...................... 351/221; 351/205; 351/243
(58) Field of Classification Search ................ 351/205, 351/243, 246, 233, 200
See application file for complete search history.

(56) References Cited

U.S. PATENT DOCUMENTS

| 6,409,345 | B1 * | 6/2002 | Molebny et al. ............. 351/212 |
| 6,525,883 | B2 * | 2/2003 | Hirohara et al. ............. 359/618 |
| 7,036,934 | B1 * | 5/2006 | Youssefi et al. ............. 351/221 |
| 2002/0041359 | A1 * | 4/2002 | Mihashi et al. ............. 351/221 |

* cited by examiner

*Primary Examiner*—Scott J. Sugarman
(74) *Attorney, Agent, or Firm*—Foley & Lardner LLP

(57) ABSTRACT

Measurement of an eye characteristic is performed more accurately and at high speed by setting a measurement condition of a light receiving optical system with a long focal point or high sensitivity on the basis of an optical characteristic measured by a light receiving optical system with a short focal point or low sensitivity or high density. The optical characteristic of the subject eye is obtained on the basis of an output of a first light receiving part and/or a second light receiving part, and a change direction of the beam is estimated on the basis of an output signal from the second light receiving part.

28 Claims, 10 Drawing Sheets $$\begin{bmatrix}
i & 2j-i & \\
0 & 0 & 1 \\
1 & -1 & r\sin(t) \\
1 & 1 & \cos(t)\,r \\
2 & -2 & r^2\sin(2t) \\
2 & 0 & 2r^2-1 \\
2 & 2 & r^2\cos(2t) \\
3 & -3 & r^3\sin(3t) \\
3 & -1 & (3r^3-2r)\sin(t) \\
3 & 1 & (3r^3-2r)\cos(t) \\
3 & 3 & r^3\cos(3t) \\
4 & -4 & r^4\sin(4t) \\
4 & -2 & (4r^4-3r^2)\sin(2t) \\
4 & 0 & 6r^4-6r^2+1 \\
4 & 2 & (4r^4-3r^2)\cos(2t) \\
4 & 4 & r^4\cos(4t) \\
5 & -5 & r^5\sin(5t) \\
5 & -3 & (5r^5-4r^3)\sin(3t) \\
5 & -1 & (10r^5-12r^3+3r)\sin(t) \\
5 & 1 & (10r^5-12r^3+3r)\cos(t) \\
5 & 3 & (5r^5-4r^3)\cos(3t) \\
5 & 5 & r^5\cos(5t) \\
6 & -6 & r^6\sin(6t) \\
6 & -4 & (6r^6-5r^4)\sin(4t) \\
6 & -2 & (15r^6-20r^4+6r^2)\sin(2t) \\
6 & 0 & 20r^6-30r^4+12r^2-1 \\
6 & 2 & (15r^6-20r^4+6r^2)\cos(2t) \\
6 & 4 & (6r^6-5r^4)\cos(4t) \\
6 & 6 & r^6\cos(6t)
\end{bmatrix}$$

FIG. 9

$$\begin{bmatrix}
i & 2j-i & \\
0 & 0 & 1 \\
1 & -1 & y \\
1 & 1 & x \\
2 & -2 & 2yx \\
2 & 0 & 2x^2 + 2y^2 - 1 \\
2 & 2 & x^2 - y^2 \\
3 & -3 & 3yx^2 - y^3 \\
3 & -1 & 3yx^2 + 3y^3 - 2y \\
3 & 1 & 3x^3 + 3xy^2 - 2x \\
3 & 3 & x^3 - 3xy^2 \\
4 & -4 & 4yx^3 - 4y^3 x \\
4 & -2 & 8yx^3 + 8y^3 x - 6yx \\
4 & 0 & 6x^4 + 12x^2 y^2 + 6y^4 - 6x^2 - 6y^2 + 1 \\
4 & 2 & 4x^4 - 4y^4 - 3x^2 + 3y^2 \\
4 & 4 & x^4 - 6x^2 y^2 + y^4 \\
5 & -5 & 5yx^4 - 10y^3 x^2 + y^5 \\
5 & -3 & 15yx^4 + 10y^3 x^2 - 5y^5 - 12yx^2 + 4y^3 \\
5 & -1 & 10yx^4 + 20y^3 x^2 + 10y^5 - 12yx^2 - 12y^3 + 3y \\
5 & 1 & 10x^5 + 20x^3 y^2 + 10xy^4 - 12x^3 - 12xy^2 + 3x \\
5 & 3 & 5x^5 - 10x^3 y^2 - 15xy^4 - 4x^3 + 12xy^2 \\
5 & 5 & x^5 - 10x^3 y^2 + 5xy^4 \\
6 & -6 & 6yx^5 - 20y^3 x^3 + 6y^5 x \\
6 & -4 & 24yx^5 - 24y^5 x - 20yx^3 + 20y^3 x \\
6 & -2 & 30yx^5 + 60y^3 x^3 + 30y^5 x - 40yx^3 - 40y^3 x + 12yx \\
6 & 0 & 20x^6 + 60x^4 y^2 + 60x^2 y^4 + 20y^6 - 30x^4 - 60x^2 y^2 - 30y^4 + 12x^2 + 12y^2 - 1 \\
6 & 2 & 15x^6 + 15x^4 y^2 - 15x^2 y^4 - 15y^6 - 20x^4 + 20y^4 + 6x^2 - 6y^2 \\
6 & 4 & 6x^6 - 30x^4 y^2 - 30x^2 y^4 + 6y^6 - 5x^4 + 30x^2 y^2 - 5y^4 \\
6 & 6 & x^6 - 15x^4 y^2 + 15x^2 y^4 - y^6 \\
\end{bmatrix}$$

FIG. 10

EYE CHARACTERISTIC MEASURING APPARATUS

BACKGROUND OF THE INVENTION

The present invention relates to an eye characteristic measuring apparatus, and particularly to an eye characteristic measuring apparatus for measuring an optical characteristic of a subject eye precisely and at high speed with plural sensitivities by using a wavefront sensor.

As a conventional corneal shape measuring apparatus, there is known an apparatus which projects an index, obtains an imaging position of the index, and measures a corneal shape. Besides, as an apparatus for measuring an optical characteristic of an eye, whose patent application was filed by the present assignee, there exists an apparatus in which pint adjustment of an illuminating optical system is performed through a received light level of a light receiving part, and pint adjustment of a light receiving optical system is performed on the basis of an optical characteristic (S) obtained from the output of the light receiving part, or an apparatus which receives converted beams from a conversion member, the number of which is smaller than that at the measurement, and performs an adjustment (Japanese Patent Application No. 9-137630 and No. 2000-321509).

Besides, there is proposed an eye characteristic measuring apparatus which measures wavefront aberrations of a subject eye more efficiently and suitably and displays them irrespective of the state of the subject eye (Japanese Patent Application No. 2001-388965 and No. 2001-376717). In this apparatus, a first illuminating optical system illuminates a minute area on a retina of a subject eye with a first light flux from a first light source part. A first light receiving optical system guides a part of a light flux reflected and returned from the retina of the subject eye through a first conversion member (Hartmann plate). Peak extraction of spot images is carried out on the basis of a first signal from the first light receiving part, and a column number of a lattice point is decided from the vicinity of the central axis in the horizontal direction on the basis of the extracted peak of the spot image, and then, a row number is decided on the basis of the spot image position of the decided column number, so that lattice point coordinates are decided. An arithmetic part carries out an operation on the optical characteristic of the subject eye on the basis of the lattice point coordinates of the respective spots.

However, in an apparatus for measuring an optical characteristic of a subject eye having aberrations, in a case where an aberration amount is large, a variation amount of a spot image becomes large, and an accurate measurement has been sometimes difficult.

SUMMARY OF THE INVENTION

In view of the above, an object of the invention is to perform, in a case where an optical characteristic of a subject eye is precisely measured, measurement of the eye characteristic more accurately and at higher speed by setting a measurement condition (lower-order aberrations such as refractive power, higher-order aberrations) of a light receiving optical system having a long focal point or high sensitivity (high magnification) on the basis of an optical characteristic measured by a light receiving optical system having a short focal point or low sensitivity or high density (low magnification). Besides, another object of the invention is to provide an eye characteristic measuring apparatus which can use measurement of a short focus version of a Hartmann shack for rough measurement.

Besides, an object of the invention is to provide an eye characteristic measuring apparatus which realizes following exemplifications.

1. Since a Hartmann image of a short focal point is used, measurement sensitivity is low, and a wide measurement range with respect to the refractive power is obtained. Since one of objects of an existing rough measurement is to perform wide refractive power measurement to move a lens and to prepare for precise measurement, first of all, the measurement with the short focal point also satisfies this.

2. Differently from a conventional rough measurement, aberration measurement is also enabled.

3. By the aberration measurement with the short focal point, the following becomes possible.

A. Almost real-time output is possible, and a dynamic change of an ocular refraction state by adjustment or the like can be measured in real time.

B. Although the precision may be sacrificed in some degree, a large aberration change can also be measured.

C. Information obtained by the rough measurement can be used in the processing of the high precision measurement. For example, recognition of a point image requires an advanced image processing technique or is sometimes impossible in the high precision measurement with the long focal distance, however, since a rough distortion of an image can be estimated by the rough measurement, the image processing and image recognition at the time of the high precision measurement can be performed correctly, and a contribution toward full automation of these processings is also made. Besides, an erroneous operation is also eliminated. It is also possible to estimate a portion where a measurement point is missing.

D. When the same light quantity as that in the long focal point is to be obtained by shortening the focal point, a small lens diameter is sufficient, and as a result, lenses can be made to have a high density, and the following becomes possible.

(1) Even if a pupil diameter is small, a large number of points can be measured, so that an analysis is possible up to a higher order aberrations (at the judgment of a permissible range, enablement and disablement of analysis due to the pupil diameter is also judged).

(2) Since the large number of points are obtained, it becomes possible to perform a higher order analysis and more accurately perform an analysis in the vicinity of a periphery.

(3) Since the high density is obtained, fitting precision to a discontinuous wavefront becomes excellent, and a higher order analysis is possible.

E. Since the measurement with the low sensitivity and the short focal point is also performed, an eye having a large aberration which can not be measured at the high sensitivity, can also be measured, and the measurement range can be widened.

F. In the case where a change of aberration is large according to a region in one measurement result, and a region where measurement can be performed with high sensitivity and a region where measurement can not be performed are mixed, it is also possible to combine the results of the short focal point and the high sensitivity (barycentric point which could not be measured with high sensitivity is reproduced from the result of the short focal point, and Zernike analysis including that point is carried out at the time of analysis of the high sensitivity).

According to first solving means of the invention, an eye characteristic measuring apparatus comprises a light source part for emitting a light flux with a first wavelength, a first illuminating optical system for illuminating a minute area on a retina of a subject eye with the light flux from the light source part, a first light receiving optical system for receiving a part of a reflected light flux reflected and returned from the retina of the subject eye through a first conversion member including a lens part having a long focal point or high sensitivity and for converting the reflected light flux into substantially at least 17 beams, a second light receiving optical system for receiving a part of the reflected light flux reflected and returned from the retina of the subject eye through a second conversion member including a lens part having a short focal point or low sensitivity or high density and for converting the reflected light flux into substantially at least 17 beams, a first light receiving part for receiving the received light flux of the first light receiving optical system, a second light receiving part for receiving the received light flux of the second light receiving optical system, a measurement condition setting part for setting a measurement condition of the first and/or the second light receiving optical system on the basis of an output signal from the second light receiving part, and an arithmetic part for obtaining an optical characteristic of the subject eye on the basis of an output of the first light receiving part and/or the second light receiving part.

According to second solving means of the invention, an eye characteristic measuring apparatus comprises a light source part for emitting a light flux with a first wavelength, a first illuminating optical system for illuminating a minute area on a retina of a subject eye with the light flux from the light source part, a first light receiving optical system for receiving a part of a reflected light flux reflected and returned from the retina of the subject eye through a first conversion member including a lens part having a long focal point or high sensitivity and for converting the reflected light flux into substantially at least 17 beams, a second light receiving optical system for receiving a part of the reflected light flux reflected and returned from the retina of the subject eye through a second conversion member including a lens part having a short focal point or low sensitivity or high density and for converting the reflected light flux into substantially at least 17 beams, a first light receiving part for receiving the received light flux of the first light receiving optical system, a second light receiving part for receiving the received light flux of the second light receiving optical system, and an arithmetic part for obtaining an optical characteristic of the subject eye on the basis of an output of the first light receiving part and/or the second light receiving part and for estimating a change direction or an arrangement of the beams by the first conversion member on the basis of the output from the second light receiving part.

BRIEF DESCRIPTION OF THE DRAWINGS

FIG. 9 is an explanatory view (1) concerning Zernike polynomials.

FIG. 10 is an explanatory view (2) concerning the Zernike polynomials.

DETAILED DESCRIPTION OF THE INVENTION

1. Structure of an Optical System

Figure 1:
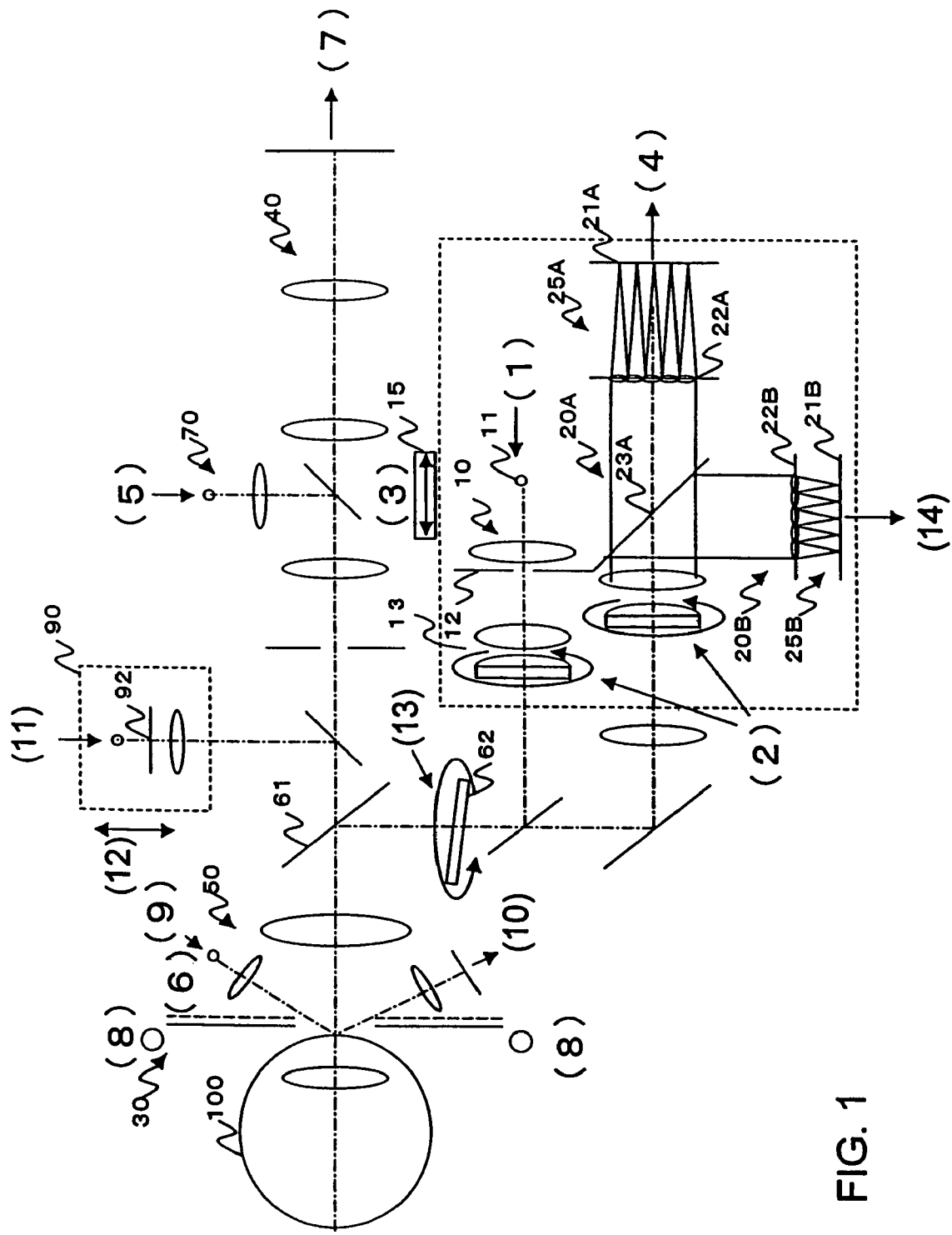
FIG. 1 is a structural view of an optical system of an eye characteristic measuring apparatus.

FIG. 1 is a structural view of an optical system of an eye characteristic measuring apparatus.

The eye characteristic measuring apparatus includes a first illuminating optical system 10, a first light source part 11, a first measurement part 25A, a second measurement part 25B, an anterior eye part illuminating part 30, an anterior eye part observation part 40, a first adjustment optical part 50, a second adjustment optical part 70, and an index optical part 90. Besides, the first measurement part 25A includes a first light receiving optical system 20A and a first light receiving part 21A, and the second measurement part 25B includes a second light receiving optical system 20B and a second light receiving part 21B. Incidentally, with respect to a subject eye 100 to be measured, a retina (fundus) and a cornea (anterior eye part) are shown.

Hereinafter, the respective parts will be described in detail.

The first illuminating optical system 10 is for illuminating a minute area on the retina of the subject eye 100 with a light flux from the first light source part 11. The first illuminating optical system 10 includes, for example, a first condensing lens, a first cylinder lens, and a first relay lens.

The first light source part 11 emits the light flux with a first wavelength. It is desirable that the first light source part 11 has a high spatial coherence and a moderate temporal coherence. Here, as an example, a super luminescence diode (SLD) is adopted for the first light source part 11, and a point light source having high luminescence can be obtained. Incidentally, the first light source part 11 is not limited to the SLD, and a laser having a high spatial coherence and a high temporal coherence can also be used by inserting a rotation diffused plate or the like to suitably lower the temporal coherence. Further, a LED having a moderate spatial coherence and a moderate temporal coherence can also be used, if light quantity is sufficient, by inserting a pinhole or the like at a position of a light source in an optical path. Besides, as a wavelength of the first light source part 11, for example, a wavelength (for example, 780 nm) of an infrared range can be used.

The first light receiving optical system 20A is for receiving and guiding, for example, the light flux reflected and returned from the retina of the subject eye 100 to the first light receiving part 21A. The first light receiving optical system 20A includes, for example, a conversion member 22A (for example, a Hartmann plate), an afocal lens, a cylinder lens, a relay lens, and a beam splitter 23A. The conversion member 22A is a wavefront conversion member including a lens part having a long focal point or high sensitivity and for converting the reflected light flux into at least 17 beams. As the conversion member 22A, plural micro Fresnel lenses disposed on a plane orthogonal to an optical axis can be used. The reflected light from the retina is condensed on the first light receiving part 21A through the conversion member 22A. The first light receiving part 21A is for receiving the light passing through the conversion member 22A from the first light receiving optical system 20A and for generating a first signal.

Similarly, the second light receiving optical system 20B is for receiving the light flux reflected and returned from the retina of the subject eye 100 and for guiding it to the second light receiving part 21B. The second light receiving optical system 20B includes, for example, a conversion member 22B (for example, a Hartmann plate), and the afocal lens, the cylinder lens, the relay lens and the beam splitter 23A shared with the first light receiving optical system 20A. The conversion member 22B is a wavefront conversion member including a lens part having a short focal point or low sensitivity or high density and for converting the reflected light flux into at least 17 beams. As the conversion member 22B, plural Fresnel lenses disposed on a plane orthogonal to an optical axis can be used. The reflected light from the retina is condensed on the second light receiving part 21B through the conversion member 22B. The second light receiving part 21B is for receiving the light passing through the conversion member 22B from the second light receiving optical system 20B and for generating a second signal.

The first measurement part 25A and the second measurement part 25B are separated by the half mirror 23. Alternatively, a mirror part is used instead of the half mirror 23, and this mirror part is moved to be inserted in the optical path, so that the first or the second measurement part 25A or 25B can be switched.

A movement part 15 moves the first illuminating optical system 10 and the first and the second light receiving optical systems 20A and 20B as a unit. For example, it is assumed that the light flux from the first light source part 11 is reflected at a condensing point, while the relation in which a signal peak at the light receiving part 21A by the reflected light becomes maximum is kept, they are moved together and moved in the direction in which the signal peak at the first light receiving part 21A becomes high, and they can be stopped at a position where the intensity becomes maximum.

With respect to the incident light on the subject eye 100 from the first light source part 11, a diaphragm 12 is made eccentric, so that vertex reflection of the lens and the cornea is prevented, and the noise can be suppressed. The diaphragm 12 has a diameter smaller than the effective range of the Hartmann plate 22A, and is designed so that so-called single path aberration measurement (method in which the aberration of an eye has an influence on only a light receiving side) can be established. A lens 13 is disposed such that a conjugated point of the retina is coincident with a front focus position so as to satisfy the above, and further, a rear focus position is coincident with the diaphragm 12 so as to satisfy a conjugated relation with respect to a pupil of the eye.

Incidentally, after the incident light beam emitted from the first light source part 11 comes to have a light path common to a measurement light beam diffused and reflected from the retina, it paraxially travels in the same way as the light beam diffused and reflected from the retina. However, in the single path measurement, the diameters of the respective light beams are different from each other, and the beam diameter of the incident light beam is set to be rather small as compared with the measurement light beam. Specifically, the beam diameter of the incident light beam is, for example, about 1 mm at the pupil position of the subject eye 100, and the beam diameter of the measurement light beam can be about 7 mm. Incidentally, by suitably disposing an optical system and enlarging the diameter of the diaphragm 12, double path measurement can also be performed.

A beam splitter 61 is constituted by, for example, a dichroic mirror for reflecting the light flux with the first wavelength. Besides, a rotary prism 62 for uniformalizing the light having reflection unevenness or the like from the retina is disposed.

The anterior eye part illuminating part 30 uses, for example, a Placido's disk, a kerato-ring or the like to illuminate the anterior eye part with a predetermined pattern. In the case of the kerato-ring, a pattern of only the vicinity of the center of curvature of the cornea can be obtained by a kerato-image. The anterior eye part observation part 40 includes, for example, a relay lens, and a light receiving part in which a telecentric diaphragm is constituted by a CCD, and observes the light flux which is originated from, for example, the pattern of the anterior eye part illuminating part 30 such as the Placido's disk or the kerato-ring and is reflected and returned from the anterior eye part of the subject eye 100. Incidentally, the telecentric diaphragm is a diaphragm for preventing the anterior eye part from blurring.

The first adjustment optical part 50 is for mainly performing a working distance adjustment, and includes a light source part, a condensing lens, and a light receiving part. Here, the working distance adjustment is performed in such a manner that for example, a parallel light flux emitted from the light source part and close to the optical axis is irradiated to the subject eye 100, and the light reflected from the subject eye 100 is received by the light receiving part through the condensing lens. Besides, in the case where the subject eye 100 is in a suitable working distance, a spot image from the light source part is formed on the optical axis of the light receiving part. On the other hand, in the case where the subject eye 100 goes out of a suitable working distance, a spot image from the light source part is formed above or below the optical axis of the light receiving part. Incidentally, since the light receiving part has only to detect a change of a light flux position on a plane containing the light source part, the optical axis, and the light receiving part, for example, a one-dimensional CCD disposed on this plane, a position sensing device (PSD) or the like can be applied.

The second adjustment optical part 70 is for performing, for example, an alignment adjustment in an XY direction, and includes an optical source part for alignment, a lens, and a beam splitter.

The index optical part 90 includes an optical path for projecting, for example, a scenery chart of the subject eye, or an index for fixation or cloudy fog, and includes a light source part (for example, a lamp), a fixed index 92, and a relay lens. The fixed index 92 can be irradiated to the retina by the light flux from the light source part, and the subject eye 100 is made to observe its image.

(Conjugated Relation)

The retina of the subject eye 100, the fixed index 92 of the index optical part 90, the first light source part 11, the first light receiving part 21A, and the second light receiving part 21B are conjugated. Besides, the ocular pupil (iris) of the subject eye 100, the rotary prism 62, the conversion members (Hartmann plates) 22A and 22B of the first and the second light receiving optical systems, and the diaphragm 12 of the first illuminating optical system 10 at the measurement light incident side are conjugated.

Figure 2:
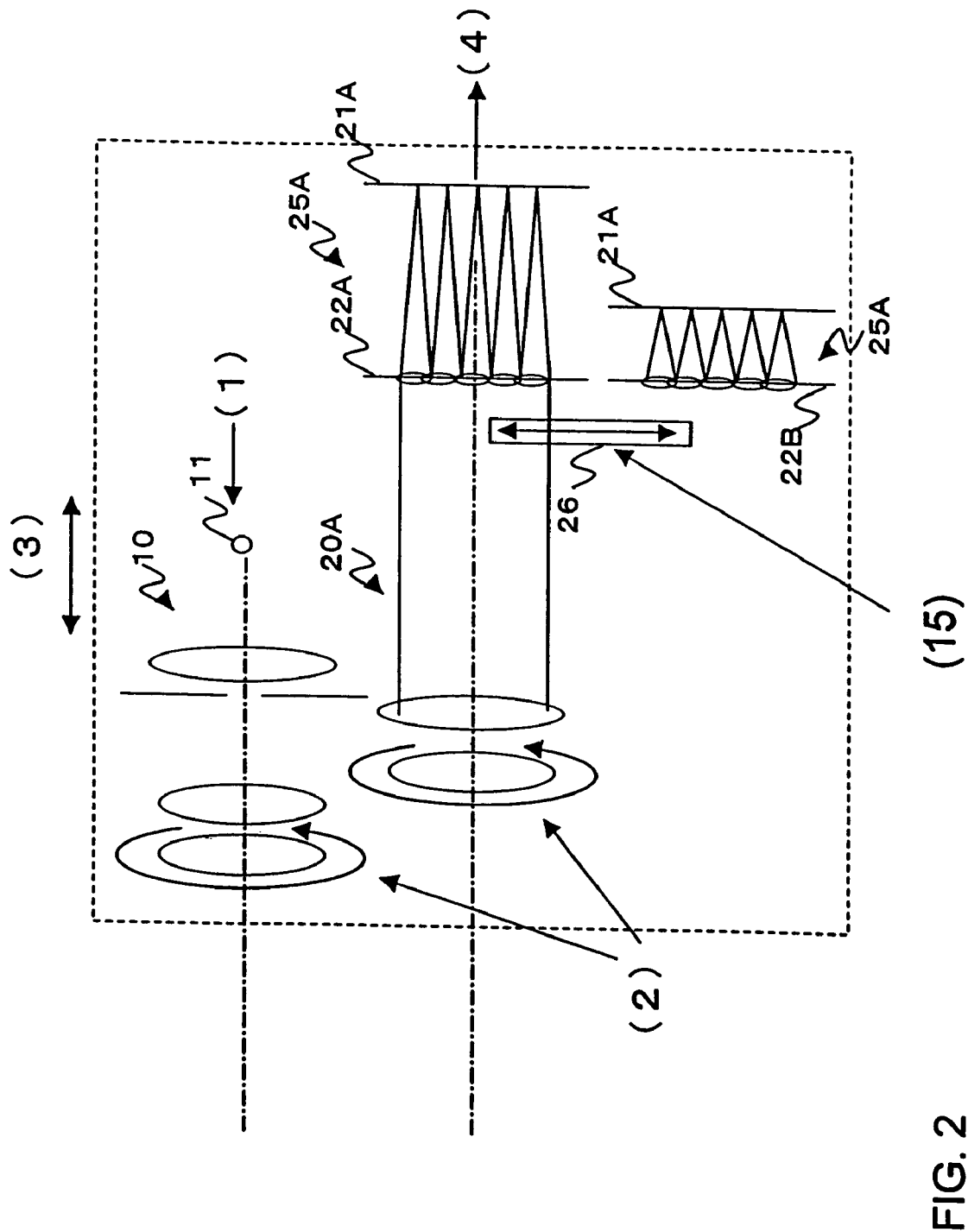
FIG. 2 is a structural view of a modified example of an optical system of the eye characteristic measuring apparatus.

FIG. 2 is a structural view of a modified example of the optical system of the eye characteristic measuring apparatus.

This drawing shows, in the eye characteristic measuring apparatus, the first illuminating optical system 10, the first light source part 11, the first light receiving optical system 20A, the first light receiving part 21A, and the second light receiving part 21B. In this example, the first measurement part 25A including the conversion member 22A and the first light receiving part 21A, or the second measurement part 25B including the conversion member 22B and the second light receiving part 21B can be moved to a light receiving position in the first light receiving optical system 20A by a movement part 26 and can be switched. In this way, the high sensitivity first measurement part 25A and the low sensitivity second measurement part 25B can be suitably switched. The movement part 26 is moved and controlled by a control signal (15) from a control part 610 and a driving part.

In the above embodiment, although the description has been given of the example in which the incident light beam has a thin single path, the invention can also be applied to an eye characteristic measuring apparatus in which the incident light beam has a thick double path. At that time, although an optical system is disposed in the structure for the double path, the measurement and calculation processing by an arithmetic part is the same.

2. Electrical Structure

Figure 3:
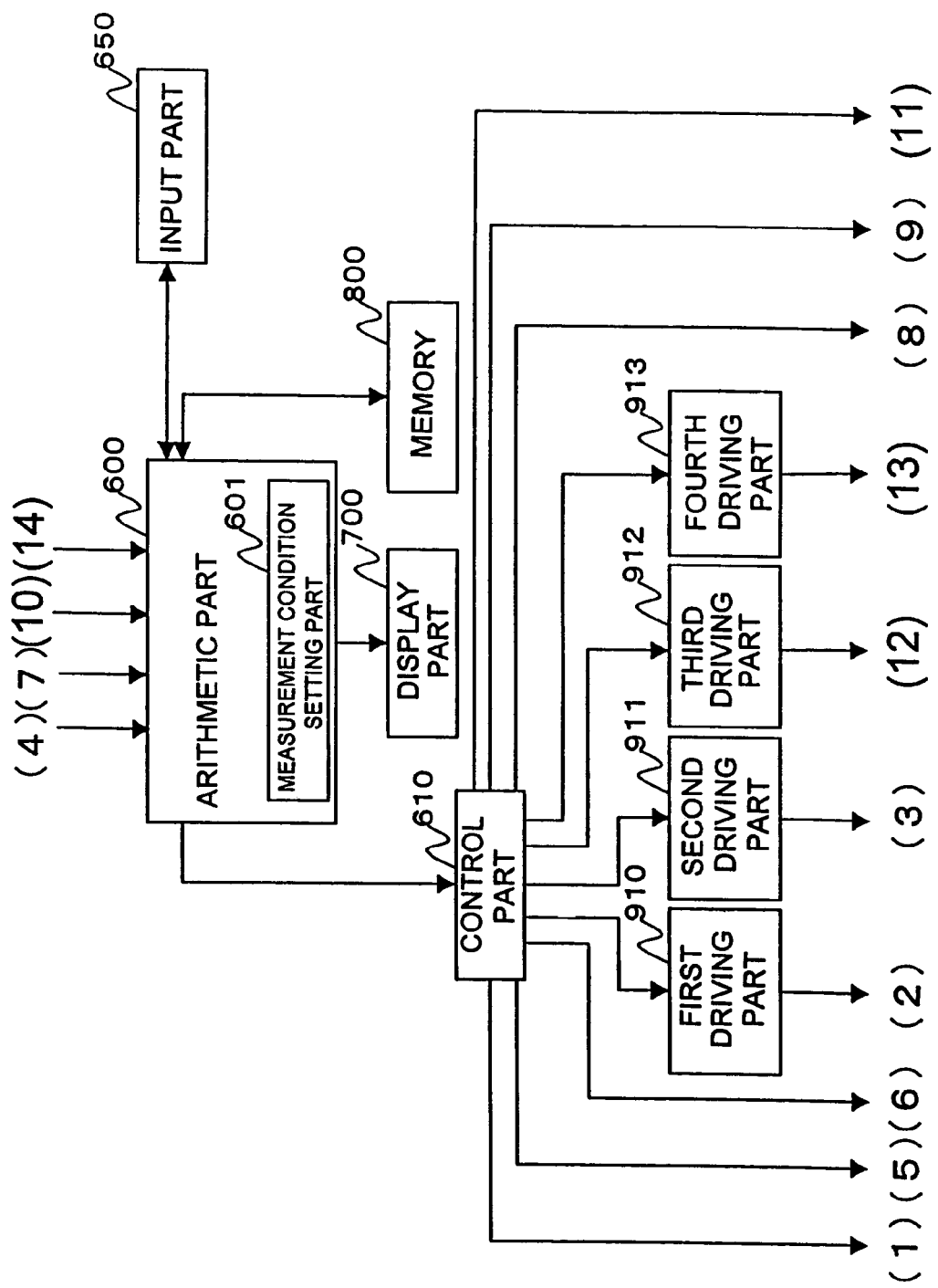
FIG. 3 is a structural view of an electrical system of the eye characteristic measuring apparatus.

FIG. 3 is a structural view of an electrical system of the eye characteristic measuring apparatus.

The structure of the electrical system of the eye characteristic measuring apparatus includes an arithmetic part 600, a control part 610, an input part 650, a display part 700, a memory 800, a first driving part 910, a second driving part 911, a third driving part 912, and a fourth driving part 913. The arithmetic part 600 includes, for example, a measurement condition setting part 601 and a processing part (a first processing part for performing precise measurement and a second processing part for performing rough measurement) for performing various eye characteristic measurements. Further, the input part 650 includes a pointing device for indicating a suitable button displayed on the display part 700, an icon, a position, a region, and the like, and a keyboard for inputting various data.

Besides, the arithmetic part 600 receives a first signal (4) from the first light receiving part 21A, a second signal (14) from the second light receiving part 21B, a signal (7) from the anterior eye part observation part 40, and a signal (10) from the first adjustment optical part 50. The arithmetic part 600 obtains the optical characteristic of the subject eye 100 based on the first signal (4) and the second signal (14) from the first and the second light receiving parts 21A and 21B and on the basis of, for example, inclination angles of the light fluxes. Besides, the arithmetic part 600 suitably outputs signals corresponding to the arithmetical operation results or other signals and data to the control part 610 for performing the control of the electrical system, the display part 700 and the memory 800.

The measurement condition setting part 601 sets measurement conditions of the first and/or the second light receiving optical system 20A and/or 20B. The measurement condition setting part 601 can be structured so as to correct the lower order aberrations with respect to the first and/or the second light receiving optical system 20A and/or 20B on the basis of the output of the second light receiving part 21B.

The control part 610 is for controlling the lighting and extinction of the first light source part 11 and for controlling the first driving part 910 to the fourth driving part 913 on the basis of the control signals from the arithmetic part 600. For example, on the basis of the signals corresponding to the arithmetical operation results in the arithmetic part 600, the control part 610 outputs a signal (1) to the first light source part 11, outputs a signal (5) to the second adjustment optical part 70, outputs a signal (6) to the anterior eye part illuminating part 30, outputs a signal (9) to the first adjustment optical part 50, outputs a signal (11) to the index optical part 90, and further outputs signals to the first driving part 910 to the sixth driving part 915.

The first driving part 910 outputs a signal (2) on the basis of the signal (4) or (14) from the first or the second light receiving part 21A or 21B inputted to the arithmetic part 600, and drives suitable lens movement means to rotate a pair of positive and negative cylinder lenses (so-called variable cross cylinder) of the first illuminating optical system, and a pair of positive and negative cylinder lenses (so-called variable cross cylinder) of the first light receiving optical system 20A (or the second light receiving optical system 20B), so as to correct an astigmatism component of the subject eye. This correction does not have to be performed.

The second driving part 911 moves the first illuminating optical system 10 and the first and the second light receiving optical systems 20A and 20B in the optical axis direction on the basis of the received light signal (4) inputted to the arithmetic part 600 from the first and/or the second light receiving part 21A and/or 21B, and outputs a signal (3) to a not-shown suitable lens movement means and drives this lens movement means.

The third driving part 912 is for moving, for example, the index optical part 90, and outputs a signal (12) to a not-shown suitable movement means and drives this movement means.

The fourth driving part 913 is for rotating the rotary prism 62, and outputs a signal (13) to a not-shown suitable lens movement means and drives this lens movement means.

3. Measurement with Short Focal Point and Long Focal Point

Figure 4B:
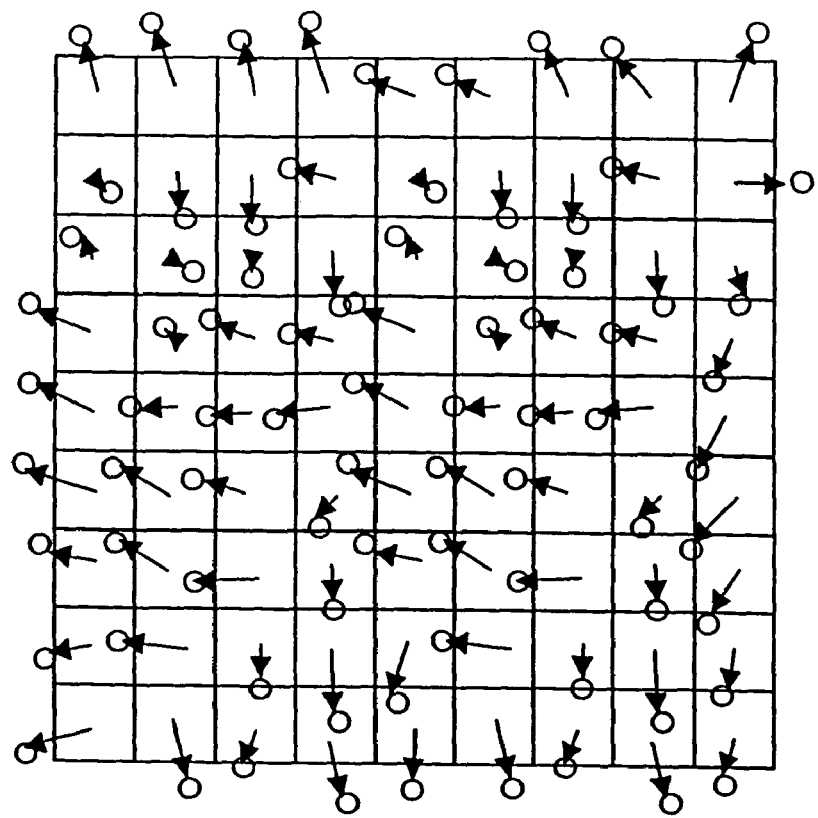
FIGS. 4A and 4B are views each showing an example of a Hartmann image.
Figure 4A:
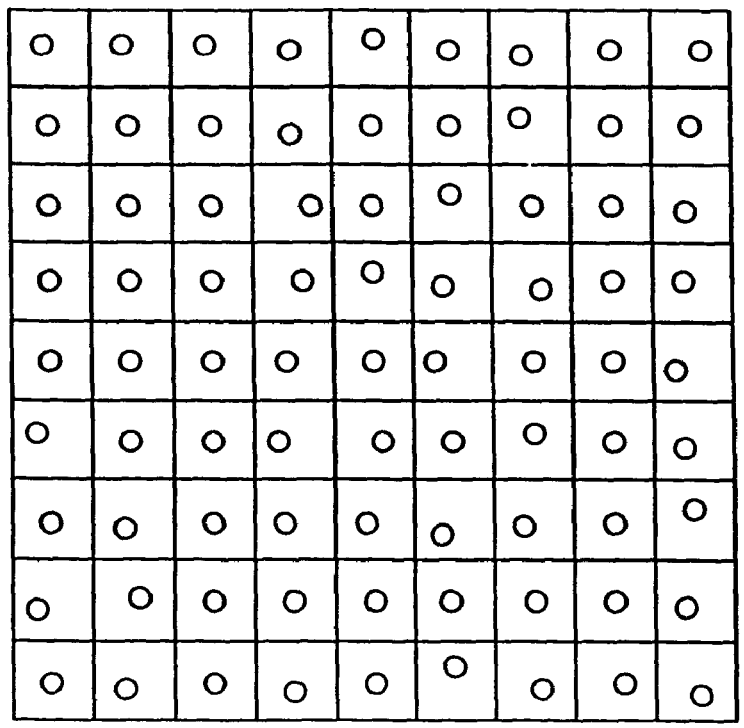

FIGS. 4A and 4B are views each showing an example of a Hartmann image. FIG. 4A shows a case where measurement is performed using the second measurement part 25B with the short focal point or the low sensitivity or the high density, and each spot exists in the range smaller than a conversion pitch of the second conversion member 22B; i.e., in the range of the Hartmann lattice of the Hartmann plate. On the other hand, FIG. 4B shows a case where measurement is performed using the first measurement part 25A with the long focal point or the high sensitivity, and there is a case where a spot exists outside the range of the Hartmann lattice.

Figure 5C:
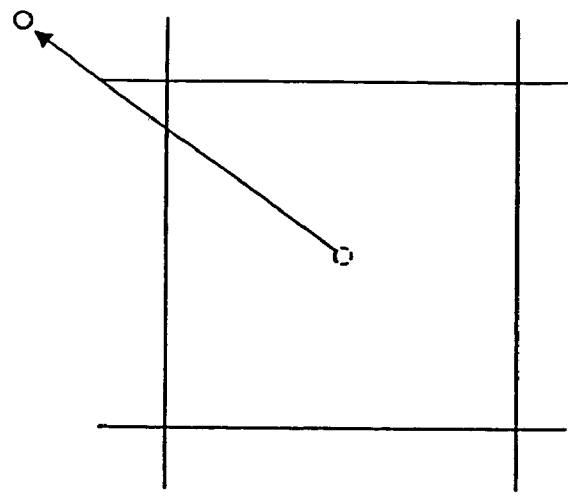
FIGS. 5A to 5C are explanatory views of measurements with a short focal point and a long focal point.
Figure 5B:
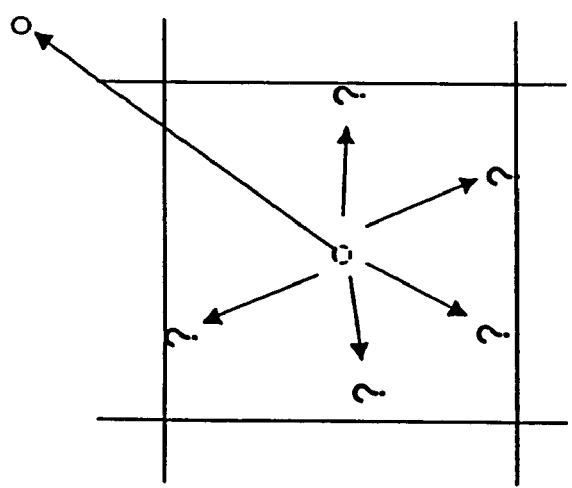
Figure 5A:
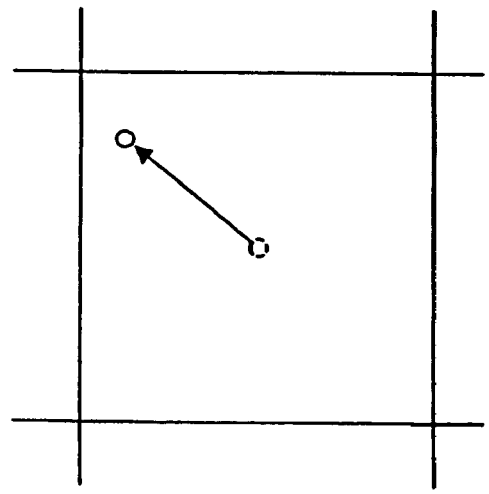

FIGS. 5A and 5B are explanatory views of the measurement with the short focal point and the long focal point. In FIG. 5A, since the measurement is performed with the short focal point or the low sensitivity or the high density, the deviation of a spot position is small, and it is within the range smaller than a conversion pitch of the second conversion member 22B; i.e., in the range of the Hartmann lattice of the Hartmann plate. Accordingly, it is easy to bring the respective spots into correspondence with the lattice points. Besides, a defective position of the spot images can be easily detected, or the detection ranges of the respective spot images do not overlap and can be uniformly detected. On the other hand, in FIG. 5B, since the measurement is performed using the first measurement part 25A with the long focal point or the high sensitivity, the deviation of the spot position is large, and the spot can exist outside the range of the Hartmann lattice. Accordingly, when the spot position is deviated very largely, there is a case where it is difficult to bring the respective spots into correspondence with the lattice points. Besides, it is very difficult to recognize a defective position of the spot images. Then, in this embodiment, as shown in FIG. 5C, the measurement is performed with the short focal point or the low sensitivity or the high density, and as a result, since a movement direction and a movement amount are known in some degree, in the case where the measurement is performed with the long focal point or the high sensitivity, the results are used to make it easy to bring the respective spots into correspondence with the lattice points.

4. Eye Characteristic Measurement

Figure 6:
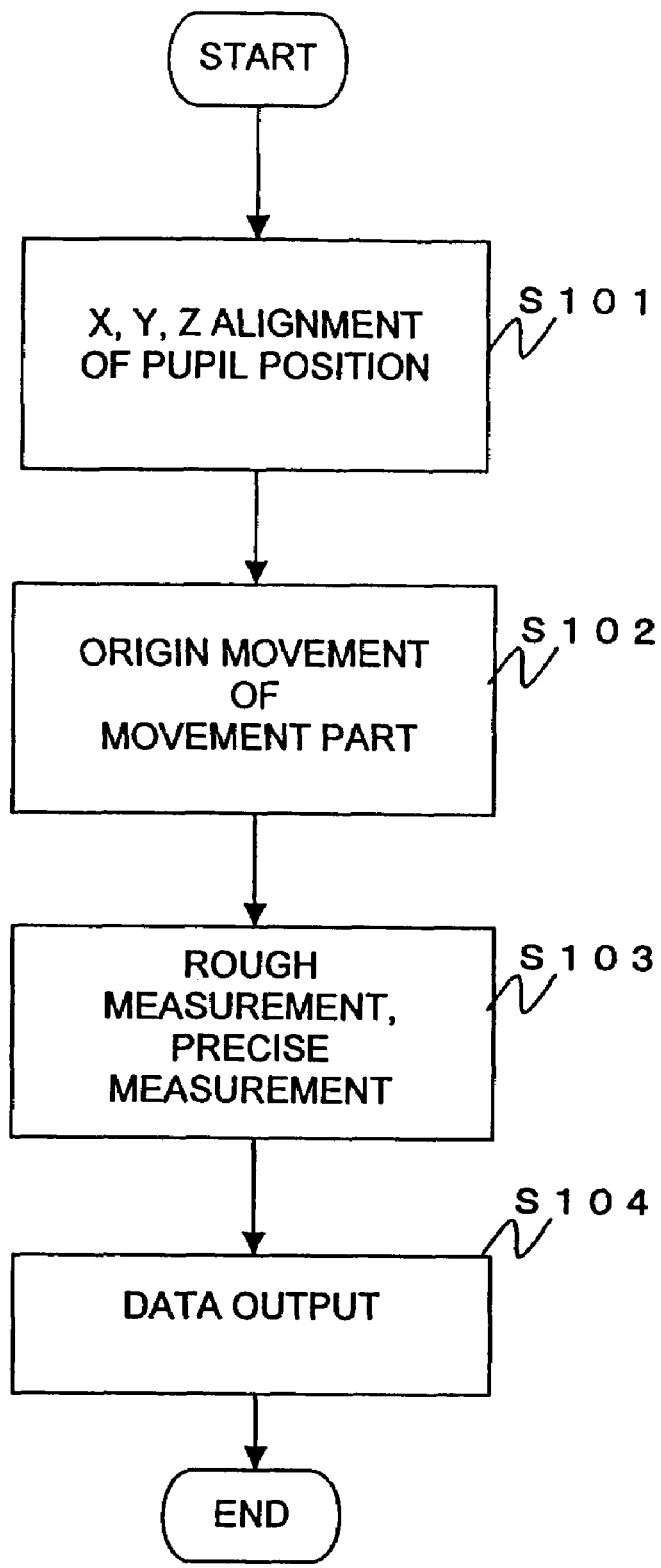
FIG. 6 is a flowchart of an eye characteristic measurement.

FIG. 6 is a flowchart of an eye characteristic measurement.

First, the eye characteristic measuring apparatus aligns X, Y and Z axes of the pupil position of the subject eye (S101). Next, the origin movement of the movement part of the measuring apparatus is performed (S102). For example, the Hartmann plate, the Placido's disk or the like is matched to zero diopter. The arithmetic part 600 measures the eye characteristic data of the ocular optical system, such as all the wavefront aberrations or Zernike coefficients, on the basis of the measured received light signal (4), (14), (7) and/or (10) (S103). The arithmetic part 600 measures the eye characteristic by rough measurement and/or precise measurement as described later. The arithmetic part 600 outputs the obtained eye characteristic data to the display part 700 and the memory 240 (S104).

Figure 7:
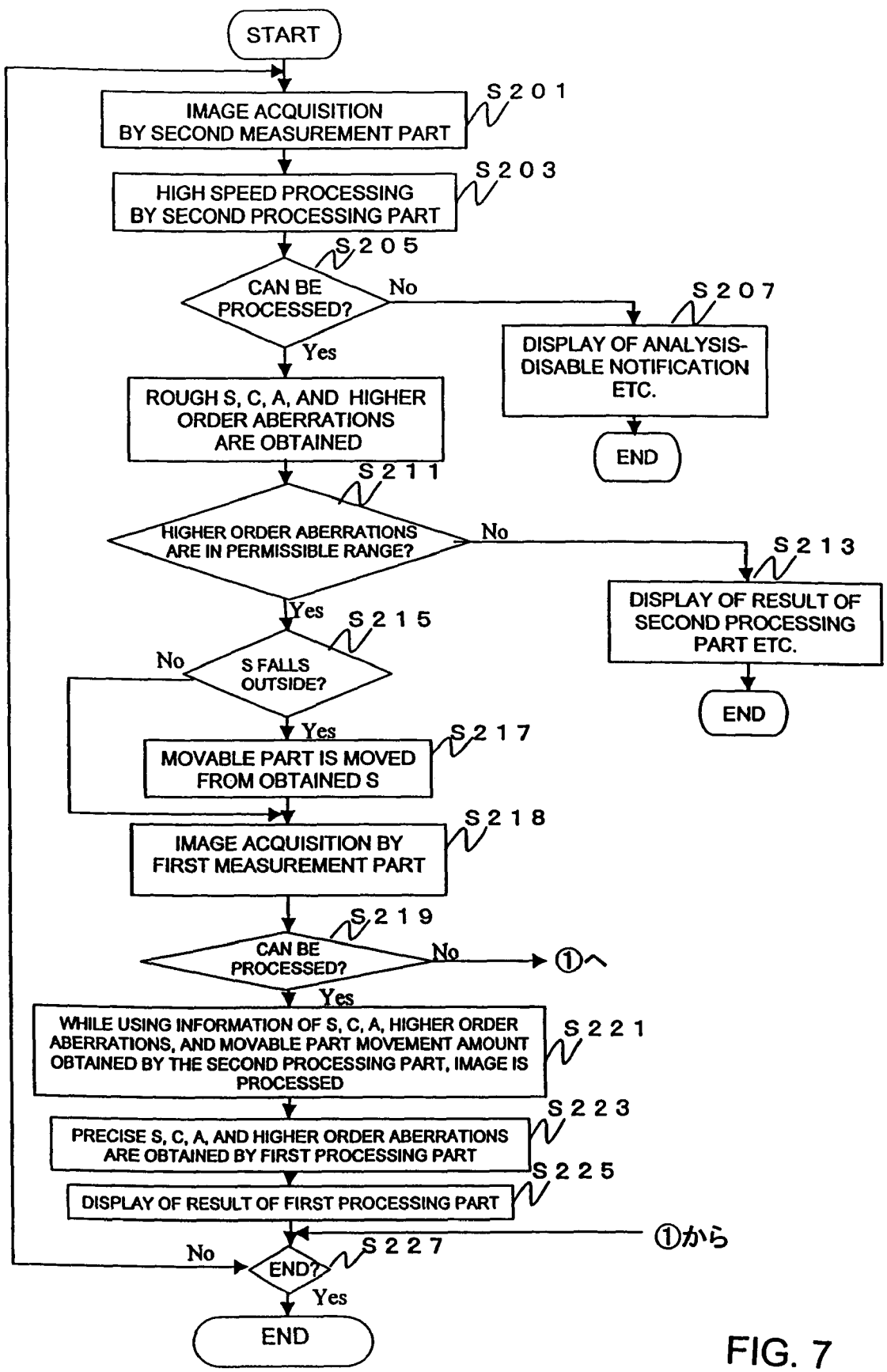
FIG. 7 is a flowchart of an eye characteristic measurement of S103.

FIG. 7 is a flowchart of the eye characteristic measurement of the step S103.

The arithmetic part 600 acquires the Hartmann image of the short focal point or the low sensitivity or the high density by the second measurement part 25B (S201). Next, the arithmetic part 600 calculates and processes the eye characteristic at high speed by the second processing part on the basis of the acquired image (S203). That is, the arithmetic part 600 detects a barycentric point of a spot image, and finds out a barycentric position corresponding to the spot in a rectangular area with the barycentric point at non-aberration as the center so that correspondences are established so as to enable high speed.

Here, a case (rough measurement) in which the second measurement part 25B is used to perform the measurement with the short focal point or the low sensitivity or the high density will be described.

The arithmetic part 600 obtains a movement amount of a point image from a picture image of the second measurement part 25B, and makes the movement amount of the i-th point image $\Delta xi$, $\Delta yi$. This is made not to exceed a determined cell as explained in FIGS. 4A and 4B or FIGS. 5A to 5C. This is normally satisfied since the distance between the second conversion member (Hartmann plate) 22B and the second light receiving part (CCD) 21B is small. On the contrary, an aberration exceeding this goes out of the measurement object of the apparatus. This movement amount and the wavefront aberrations W are correlated by a following partial differential equation.

$$\frac{\partial W(X, Y)}{\partial X} = \frac{\Delta x}{f},$$

$$\frac{\partial W(X, Y)}{\partial Y} = \frac{\Delta y}{f}$$

(f: distance between the Hartmann plate of the second measurement part 25B and the CCD).

Here, when the wavefront W is expressed by an expansion using Zernike polynomial expressions $Z_i^{2j-1}$, the following is obtained.

$$W(X, Y) = \sum_{i=0}^{n} \sum_{j=0}^{i} c_i^{2j-i} Z_i^{2j-i}(X, Y)$$

Respective values of the Zernike coefficients $c_n^m$ can be obtained using the above two expressions and measurement values relating to $\Delta x$, $\Delta y$ (thus, including X and Y) obtained by the measurement. In this method, since the point image exists in a certain decided range, a very high speed processing is possible.

Incidentally, FIGS. 9 and 10 are explanatory views (1) and (2) concerning the Zernike polynomial expressions.

Here, the arithmetic part 600 judges whether the measurement processing is possible (S205). The arithmetic part 600 makes the judgment on the basis of one or a plurality of predetermined suitable conditions, for example, a predetermined number of barycentric positions or more (for example, one third) can not be taken, blur of each of the point images is large (for example, 20 times or more as large as that at the time of non-aberration), or there are a predetermined number of points or more which can not be detected since they can not be separated from the adjacent spot images.

Here, in the case where the processing is impossible, the arithmetic part 600 displays analysis disable notification, and if necessary, displays a second Hartmann image from the second light receiving part (S207), and on the other hand, in the case where the processing is possible, the arithmetic part 600 obtains, as described above, a rough refractive power S, an degree of astigmatism C, an astigmatism axis A, and a higher order aberrations (S209). That is, the arithmetic part 600 can obtain the refractive power S, the degree of astigmatism C, the astigmatism axis A, and the higher order aberrations by the obtained Zernike coefficients $C_n^m$ and the arrangement of the optical system (information, for example, where a movement position is located under an initial condition) and by using an already-known method. The arithmetic part 600 can obtain the refractive power S, the degree of astigmatism C, and the astigmatism axis A from secondary terms of the Zernike coefficients as in the following expression. The arithmetic part 600 suitably stores values obtained by the rough measurement in the memory.

$$SE = S_{move} - 4 \cdot \frac{c_2^0}{r^2}$$

$$S = SE - \frac{1}{2} \cdot C$$

-continued $$C = -4 \cdot \frac{\sqrt{(c_2^{-2})^2 + (c_2^2)^2}}{r^2}$$

$$A = \tan^{-1}\left(\frac{c_2^{-2}}{c_2^2}\right) \cdot \frac{1}{2} \cdot \frac{180}{\pi} + 90$$

(where, SE: equivalent refractive power, $S_{move}$: refractive power for fixation movement, r: pupil radius mm)

Next, the arithmetic part 600 judges whether the higher order aberrations are within a permissible range (S211). For example, when the high sensitivity measurement is performed with a predetermined aberration amount or more, and when it appears that branching of point images is difficult, it falls outside the permissible range. Then, the arithmetic part 600 calculates, for example, the respective barycentric positions of Hartmann images expected when the high sensitivity measurement is performed from the wavefront aberrations analyzed with this low sensitivity, and when there is one which is separated from the adjacent point by a predetermined range (for example, 5 pixels or less), it can be regarded as falling outside the permissible range. Incidentally, the barycentric position is obtained by calculating the inclination of the wavefront W(X, Y) at (X, Y) (see the numerical expressions 1 and 2) and obtaining position on the CCD of the first light receiving part 21A. Besides, when the pupil diameter is smaller than a predetermined size at the low sensitivity (for example, when less than φ4 mm at photopic vision), or the number of barycentric points converted at the high sensitivity with respect to the order of the aberration analysis is small, the case can be made to apply to this. At step S211, in the case where it is not in the permissible range, the arithmetic part 600 reads out the result according to the rough measurement of the second processing part, and displays the result, and if necessary, the second Hartmann image from the second light receiving part (S213).

On the other hand, at the step S211, when it is in the permissible range, the arithmetic part 600 judges whether the lower order aberrations such as the refractive power S are out of the permissible range (S215). For example, when the movable part movement amount is in the permissible range (for example, when the refractive power S is 0.01 D or less), the arithmetic part 600 can judge that it is not out of the permissible range. When the lower order aberrations such as the refractive power S are out of the permissible range, the measurement condition setting part 601 of the arithmetic part 600 outputs the signal (3) by the control part 610 from the lower order aberrations, such as the refractive power S, obtained by the second measurement part 25B, and corrects the lower order aberrations by moving the movement part 15 (S217). Here, the arithmetic part 600 can move for a distance equivalent to the movement amount of the movement part 15 decided from the lower order aberrations such as the refractive power S of the subject eye. Especially, since the lower order aberrations are corrected using the spot obtained by the second conversion member, the condition becomes more suitable for measurement at the measurement after the movement.

After the step S215 or S217, the arithmetic part 600 acquires the Hartmann picture image of the long focal point or the high sensitivity by the first measurement part 25A (S218). The arithmetic part 600 judges whether the processing can be performed similarly to the step S205 (S219). At step S219, in the case where the processing is possible, the arithmetic part 600 uses the information of the refractive power S, the degree of astigmatism C, the astigmatism axis A, the higher order aberrations, and the movement amount of the movement part, obtained by the second processing part, that is, takes the spherical component corresponding to the movement amount of the movement part into consideration, and processes the picture image and performs the precise measurement (S221).

Here, a case (precise measurement) in which the first measurement part 25A is used to perform the measurement with the long focal point or the high sensitivity will be described. The arithmetic part 600 can estimate the point image obtained from the first measurement part 25A from the previous result of the rough measurement obtained by the second measurement part 25B. That is, with respect to the previous expression, a similar relation is established as in the following expression except that the distance between the Hartmann plate and the CCD or the deviation of the point image varies according to the focal point or the sensitivity of the first or the second measurement part 25A or 25B.

$$\frac{\partial W(X, Y)}{\partial X} = \frac{\Delta \hat{x}}{F},$$

$$\frac{\partial W(X, Y)}{\partial Y} = \frac{\Delta \hat{y}}{F}$$

$$W(X, Y) = \sum_{i=0}^{n} \sum_{j=0}^{i} c_i^{2j-i} Z_i^{2j-i}(X, Y)$$

(F: distance between the Hartmann plate of the first measurement part 25A and the CCD)

Especially, the wavefront aberrations W and the Zernike coefficients $c_i^{2j-i}$ must be essentially the same though there is a difference according to the measurement accuracy. (However, when the point image movement amount of the precise measurement is calculated from the rough measurement, the spherical component corresponding to the movement amount of the movement part, and if the astigmatism component is corrected, the astigmatism component corresponding to the correction amount by a pair of positive and negative cylinder lenses (so-called variable cross cylinder) are corrected when the image is acquired by the first measurement part, and therefore, the wavefront in which the correction component is removed must be observed. Thus, if the correction concerns only the spherical component, i≠2 and j≠0, and if the correction of the astigmatism component is also performed, i≠2) Then, by conversely using this expression, with respect to the k-th spot image, the point image movement amount $\Delta \hat{x}_k$, $\Delta \hat{y}_k$ of the precise measurement can be calculated from the rough measurement. Actually, it can be measured from the following expression.

$$\Delta \hat{x}_k = \frac{\partial}{\partial X} \sum c_n^m Z_n^m(X_k, Y_k) \cdot F = \sum c_n^m \frac{\partial}{\partial X} Z_n^m(X_k, Y_k) \cdot F$$

$$\Delta \hat{y}_k = \frac{\partial}{\partial Y} \sum c_n^m Z_n^m(X_k, Y_k) \cdot F = \sum c_n^m \frac{\partial}{\partial Y} Z_n^m(X_k, Y_k) \cdot F$$

By this, in the first place, it is also possible to judge whether the first processing can be performed.

In this way, the arithmetic part 600 obtains the precise refractive power S, the degree of astigmatism C, the astigmatism axis A, and the higher order aberrations (S223). Further, the arithmetic part 600 displays the result of the first processing part, and if necessary, the second Hartmann image from the first and/or the second light receiving part on the display part 700, and stores them in the memory (S225). The arithmetic part 600 judges whether the processing is ended (S227), and as the need arises, it returns to the step S201, repeats the processing, and is ended.

Figure 8:
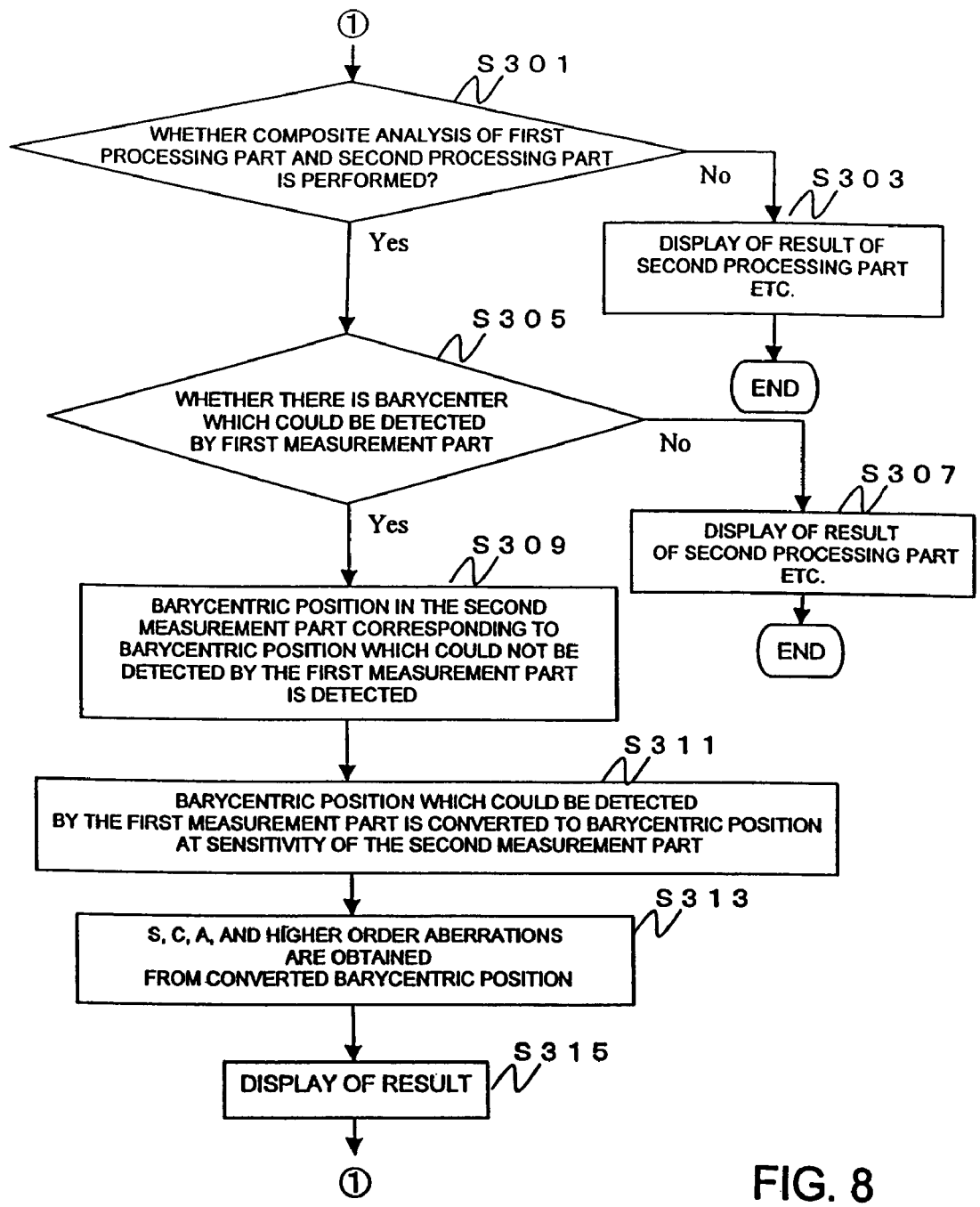
FIG. 8 is a flowchart of a subroutine in a case where an image obtained by a first measurement part 25A can not be processed.

FIG. 8 is a flowchart of a subroutine of a case where the picture image acquired by the first measurement part 25A can not be processed.

In the case where it is judged at the step S219 that the processing is impossible, the arithmetic part 600 judges whether composite analysis of the first processing part and the second processing part is to be performed (S301). At this time, when a default value is previously set in the memory, or is inputted by the input part 650, so that the arithmetic part 600 can select a processing.

In the case where the composite analysis is not performed, the arithmetic part 600 reads out the result of the second processing part from the memory, and displays the result, and if necessary, the second Hartmann image from the second light receiving part. On the other hand, in the case where the composite analysis is performed, the arithmetic part 600 judges whether there are a predetermined number of barycenters which can be detected by the first measurement part 25A (S305). Here, in the case where the predetermined number of barycenters could not be detected, the arithmetic part 600 reads out the result from the memory, and displays the result, and if necessary, the second Hartmann image from the second light receiving part (S307). On the other hand, in the case where the predetermined number of barycenters could be detected, the arithmetic part 600 detects the barycentric position according to the second measurement part 25B corresponding to the barycentric position which could not be detected by the first measurement part 25A (S309). Next, the arithmetic part 600 converts the barycentric position which could be detected by the second measurement part 25B to the barycentric position at the sensitivity of the first measurement part 25A (S311). That is, in the case where the change of the aberration is large according to the region in one measurement result, and the region which can be measured with high sensitivity and the region which can not be measured are mixed, the results of the short focal point and the high sensitivity are combined. At this step, the arithmetic part 600 reproduces the barycentric point which could not be measured with the high sensitivity from the result of the short focal point, and the Zernike analysis including that point is performed at the time of the analysis with the high sensitivity (incidentally, with respect to the conversion method, see the numerical expression 5, etc.). The arithmetic part 600 obtains the refractive power S, the degree of astigmatism C, the astigmatism axis A, and the higher order aberrations from the converted barycentric position (S313). The arithmetic part 600 displays the result of the composite analysis, and if necessary, the second Hartmann image from the first and/or the second light receiving part on the display part 700, stores them in the memory (S315), and returns to the step S227 of FIG. 7.

At the step S311, the barycentric position which could be detected by the first measurement part 25A may be converted to the barycentric position with the sensitivity of the second measurement part 25B.

According to the present invention, as described above, in the case where the optical characteristic of the subject eye is precisely measured, the measurement of the eye characteristic can be performed more accurately and at higher speed by setting the measurement condition (lower order aberrations such as refractive power, higher order aberrations) of the light receiving optical system having the long focal point or the high sensitivity (high magnification) on the basis of the optical characteristic measured by the light receiving optical system having the short focal point or the low sensitivity or the high density (low magnification). Besides, according to the invention, it is possible to provide the eye characteristic measuring apparatus which can use the measurement of the short focus version of the Hartmann shack for the rough measurement.

Besides, the invention has effects as exemplified below.

1. Since the Hartmann image of the short focal point is used, the measurement sensitivity is low, and the wide measurement range with respect to the refractive power is obtained. Since one of objects of an existing rough measurement is also to perform the wide refractive power measurement to move a lens and to prepare for the precise measurement, first of all, the measurement with the short focal point also satisfies this.

2. Differently from a conventional rough measurement, the aberration measurement is also be enabled.

3. By the aberration measurement with the short focal point, the following becomes possible.

A. Almost real-time output can be enabled, and the dynamic change of an ocular refraction state by adjustment or the like can be measured in real time.

B. Although the precision is sacrificed in some degree, a large aberration change can also be measured.

C. Information obtained by the rough measurement can be used in the processing of the high precision measurement. For example, the recognition of a point image requires an advanced image processing technique or is sometimes impossible in the high precision measurement with the long focal distance, however, since the rough distortion of the image can be estimated by the rough measurement, the image processing and image recognition at the time of the high precision measurement can be performed correctly, and a contribution toward the full automation of these processings can be made. Besides, an erroneous operation is also eliminated. It is also possible to estimate a portion where a measurement point is missing.

D. The density can be increased by shortening the focal point, and the following becomes possible.

(1) Even if a pupil diameter is small, a large number of points can be measured, so that an analysis is possible up to a higher order aberrations (at judgment of a permissible range, enablement and disablement of the analysis due to the pupil diameter is also judged).

(2) Since the large number of points are obtained, it becomes possible to perform a higher order analysis.

(3) Since the high density is obtained, a fitting precision to a discontinuous wavefront becomes excellent, and a higher order analysis is possible.

E. Since the measurement with the low sensitivity and the short focal point is also performed, an eye having a large aberration which can not be measured at the high sensitivity, can also be measured, and the measurement range can be widened.

F. In the case where the change of aberration is large according to a region in one measurement result, and a region where measurement can be performed with high sensitivity and a region where measurement can not be performed are mixed, it is also possible to combine the results of the short focal point and the high sensitivity (barycentric point which could not be measured with high sensitivity is reproduced from the result of the short focal point, and Zernike analysis including that point is carried out at the time of analysis of the high sensitivity).

What is claimed is:

1. An eye characteristic measuring apparatus comprising:
a light source part configured to emit a light flux with a first wavelength; a first illuminating optical system configured to illuminate a minute area on a retina of a subject eye with the light flux from the light source part;
a first light receiving optical system configured to receive a part of a reflected light flux reflected and returned from the retina of the subject eye through a first conversion member including a lens part having a long focal point or first sensitivity and configured to convert the reflected light flux into substantially at least 17 beams;
a second light receiving optical system configured to receive a part of the reflected light flux reflected and returned from the retina of the subject eye through a second conversion member including a lens part having a short focal point or second sensitivity and configured to convert the reflected light flux into substantially at least 17 beams, the first sensitivity being greater than the second sensitivity;
a first light receiving part configured to receive the received light flux of the first light receiving optical system;
a second light receiving part configured to receive the received light flux of the second light receiving optical system;
a measurement condition setting part configured to set a measurement condition of the first and/or the second light receiving optical system on the basis of an output signal from the second light receiving part; and
an arithmetic part configured to obtain an optical characteristic of the subject eye on the basis of an output of the first light receiving part and/or the second light receiving part.

2. An eye characteristic measuring apparatus according to claim 1, wherein the measurement condition setting part corrects the lower order aberrations with respect to the first and/or the second light receiving optical system on the basis of the output of the second light receiving part.

3. An eye characteristic measuring apparatus according to claim 1, wherein the illuminating optical system illuminates the minute area on the retina of the subject eye with thin beams of the light flux from the light source part.

4. An eye characteristic measuring apparatus according to claim 1, wherein the illuminating optical system illuminates the minute area on the retina of the subject eye with wide beams of the light flux from the light source part.

5. An eye characteristic measuring apparatus according to claim 1, wherein the optical characteristic is obtained on the basis of the output of the second light receiving part, and as a result, when there are third or higher order aberrations with a predetermined amount or more, the arithmetic part makes a result on the basis of the output of the second light receiving part regarding the optical characteristic of the subject eye.

6. An eye characteristic measuring apparatus according to claim 2, wherein the optical characteristic is obtained on the basis of the output of the second light receiving part, and as a result, when three or higher order aberrations with a predetermined amount or more are not obtained, the measurement condition setting part changes the measurement condition of the first and/or the second light receiving optical system by the optical characteristic obtained on the basis of the second light receiving part, and the arithmetic part obtains the optical characteristic of the subject eye on the basis of the output of the first light receiving part after the change.

7. An eye characteristic measuring apparatus according to claim 2, wherein the optical characteristic is obtained on the basis of the output of the second light receiving part, and as a result, when three or higher order aberrations with a predetermined amount or more are not obtained, the measurement condition setting part changes the measurement condition of the first and/or the second light receiving optical system by the optical characteristic obtained on the basis of the second light receiving part, and the arithmetic part obtains the optical characteristic of the subject eye on the basis of the outputs of the first light receiving part and the second light receiving part after the change.

8. An eye characteristic measuring apparatus according to claim 1, wherein the arithmetic part obtains a position of a received light point in the first light receiving part on the basis of a position of a received light point in the second light receiving part with the short focal point or the second sensitivity.

9. An eye characteristic measuring apparatus according to claim 1, wherein the arithmetic part obtains a position of a received light point in the first light receiving part on the basis of a deviation direction and a deviation amount of a received light point in the second light receiving part with the short focal point or the second sensitivity.

10. An eye characteristic measuring apparatus according to claim 1, wherein the arithmetic part estimates a movement amount of a point image relating to the output of the first light receiving part by using Zernike coefficients obtained on the basis of the output of the second light receiving part.

11. An eye characteristic measuring apparatus according to claim 1, wherein in the second light receiving optical system, a change of the beam converted by the second conversion member over a measurable range is set to be smaller than a conversion pitch of the second conversion member.

12. An eye characteristic measuring apparatus according to claim 1, wherein in the second light receiving optical system, a change of the beam converted by the second conversion member over a measurable range is set to be smaller than a conversion pitch of the second conversion member, and as a result, a defective position of spot images can be easily detected, or detection ranges of the respective spot images can be uniformly detected without overlap.

13. An eye characteristic measuring apparatus according to claim 1, wherein in the first light receiving optical system, a change of the beam converted by the first conversion member over a measurable range is set to be larger than a conversion pitch of the first conversion member.

14. An eye characteristic measuring apparatus according to claim 1, further comprising a Hartmann image display part configured to receive the signal from the first light receiving part and/or the second light receiving part, and the Hartmann image display part displays a first Hartmann image according to the first conversion member including the lens part with the high sensitivity or the long focal point and/or a Hartmann image according to the second conversion member including the lens part with the second sensitivity or the short focal point.

15. An eye characteristic measuring apparatus comprising:
a light source part configured to emit a light flux with a first wavelength;

a first illuminating optical system configured to illuminate a minute area on a retina of a subject eye with the light flux from the light source part;

a first light receiving optical system configured to receive a part of a reflected light flux reflected and returned from the retina of the subject eye through a first conversion member including a lens part having a long focal point or first sensitivity and configured to convert the reflected light flux into substantially at least 17 beams;

a second light receiving optical system configured to receive a part of the reflected light flux reflected and returned from the retina of the subject eye through a second conversion member including a lens part having a short focal point or second sensitivity and configured to convert the reflected light flux into substantially at least 17 beams, the first sensitivity being greater than the second sensitivity;

a first light receiving part configured to receive the received light flux of the first light receiving optical system;

a second light receiving part configured to receive the received light flux of the second light receiving optical system; and an arithmetic part configured to obtain an optical characteristic of the subject eye on the basis of an output of the first light receiving part and/or the second light receiving part and configured to estimate a change of direction or an arrangement of the beams by the first conversion member on the basis of the output from the second light receiving part.

16. An eye characteristic measuring apparatus according to claim 15, further comprising a measurement condition setting part configured to set a measurement condition of the first and/or the second light receiving optical system, wherein the measurement condition setting part corrects lower order aberrations with respect to the first and/or the second light receiving optical system on the basis of the output of the second light receiving part.

17. An eye characteristic measuring apparatus according to claim 15, wherein the illuminating optical system illuminates the minute area on the retina of the subject eye with the thin beams of the light flux from the light source part.

18. An eye characteristic measuring apparatus according to claim 15, wherein the illuminating optical system illuminates the minute area on the retina of the subject eye with wide beams of the light flux from the light source part.

19. An eye characteristic measuring apparatus according to claim 15, wherein the optical characteristic is obtained on the basis of the output of the second light receiving part, and as a result, when there are third or higher order aberrations with a predetermined amount or more, the arithmetic part makes a result on the basis of the output of the second light receiving part regarding the optical characteristic of the subject eye.

20. An eye characteristic measuring apparatus according to claim 16, wherein the optical characteristic is obtained on the basis of the output of the second light receiving part, and as a result, when three or higher order aberrations with a predetermined amount or more are not obtained, the measurement condition setting part changes the measurement condition of the first and/or the second light receiving optical system by the optical characteristic obtained on the basis of the second light receiving part, and the arithmetic part obtains the optical characteristic of the subject eye on the basis of the output of the first light receiving part after the change.

21. An eye characteristic measuring apparatus according to claim 16, wherein the optical characteristic is obtained on the basis of the output of the second light receiving part, and as a result, when three or higher order aberrations with a predetermined amount or more are not obtained, the measurement condition setting part changes the measurement condition of the first and/or the second light receiving optical system by the optical characteristic obtained on the basis of the second light receiving part, and the arithmetic part obtains the optical characteristic of the subject eye on the basis of the outputs of the first light receiving part and the second light receiving part after the change.

22. An eye characteristic measuring apparatus according to claim 15, wherein the arithmetic part obtains a position of a received light point in the first light receiving part on the basis of a position of a received light point in the second light receiving part with the short focal point or the second sensitivity.

23. An eye characteristic measuring apparatus according to claim 15, wherein the arithmetic part obtains a position of a received light point in the first light receiving part on the basis of a deviation direction and a deviation amount of a received light point in the second light receiving part with the short focal point or the second sensitivity.

24. An eye characteristic measuring apparatus according to claim 15, wherein the arithmetic part estimates a movement amount of a point image relating to the output of the first light receiving part by using Zernike coefficients obtained on the basis of the output of the second light receiving part.

25. An eye characteristic measuring apparatus according to claim 15, wherein in the second light receiving optical system, a change of the beam converted by the second conversion member over a measurable range is set to be smaller than a conversion pitch of the second conversion member.

26. An eye characteristic measuring apparatus according to claim 15, wherein in the second light receiving optical system, a change of the beam converted by the second conversion member over a measurable range is set to be smaller than a conversion pitch of the second conversion member, and as a result, a defective position of spot images can be easily detected, or detection ranges of the respective spot images can be uniformly detected without overlap.

27. An eye characteristic measuring apparatus according to claim 15, wherein in the first light receiving optical system, a change of the beam converted by the first conversion member over a measurable range is set to be larger than a conversion pitch of the first conversion member.

28. An eye characteristic measuring apparatus according to claim 15, further comprising a Hartmann image display part configured to receive the signal from the first light receiving part and/or the second light receiving part, and the Hartmann image display part displays a first Hartmann image according to the first conversion member including the lens part with the first sensitivity or the long focal point and/or a Hartmann image according to the second conversion member including the lens part with the second sensitivity or the short focal point.

* * * * *